United States Patent [19]

O'Rourke

[11] 4,181,997
[45] Jan. 8, 1980

[54] WATER-POWERED TOOTHBRUSH WITH DENTIFRICE ATTACHMENT

[76] Inventor: James L. O'Rourke, 6351 Memorial, Detroit, Mich. 48226

[21] Appl. No.: 898,645

[22] Filed: Apr. 21, 1978

[51] Int. Cl.$^2$ ............................................. A46B 13/06
[52] U.S. Cl. ........................................ 15/24; 401/156; 401/278
[58] Field of Search .......................... 15/22 R, 24, 29; 401/152–154, 156, 157, 188 R, 270, 271, 278, 289

[56] References Cited

U.S. PATENT DOCUMENTS

| | | | |
|---|---|---|---|
| 172,067 | 1/1876 | Alexander | 15/24 |
| 1,060,524 | 4/1913 | Wolfe | 401/271 X |
| 1,108,475 | 8/1914 | Roland | 15/24 |
| 1,471,748 | 10/1923 | Miller | 15/24 |
| 2,285,865 | 6/1942 | Lowe et al. | 15/24 |
| 2,652,949 | 9/1953 | Martin | 401/152 X |
| 2,682,675 | 7/1954 | Prucha | 15/29 |
| 2,717,403 | 9/1955 | Batlas et al. | 15/29 |
| 2,790,190 | 4/1957 | Mastrandrea | 401/188 X |
| 2,841,806 | 7/1958 | Blasi | 15/24 |
| 2,855,619 | 10/1958 | Graham | 401/188 X |
| 3,056,151 | 10/1962 | Vlacancich | 15/29 |
| 3,864,047 | 2/1975 | Sherrod | 401/278 |

FOREIGN PATENT DOCUMENTS 1031993 3/1953 France .......................................... 15/29

Primary Examiner—Edward L. Roberts
Attorney, Agent, or Firm—Whittemore, Hulbert & Belknap

[57] ABSTRACT

A tooth-brushing device comprising a brushing unit provided with rotating brushes, and a dentifrice-carrying cartridge unit. The cartridge unit is attachable to a water faucet and supports an impeller operated by water pressure to rotate the brushes. The cartridge unit also has a passage for conducting water from the faucet to the rotating brushes. The cartridge unit supports a disposable dentifrice tube which is squeezed by the pressure of water from the faucet to force dentifrice from the tube to the brushes.

15 Claims, 12 Drawing Figures

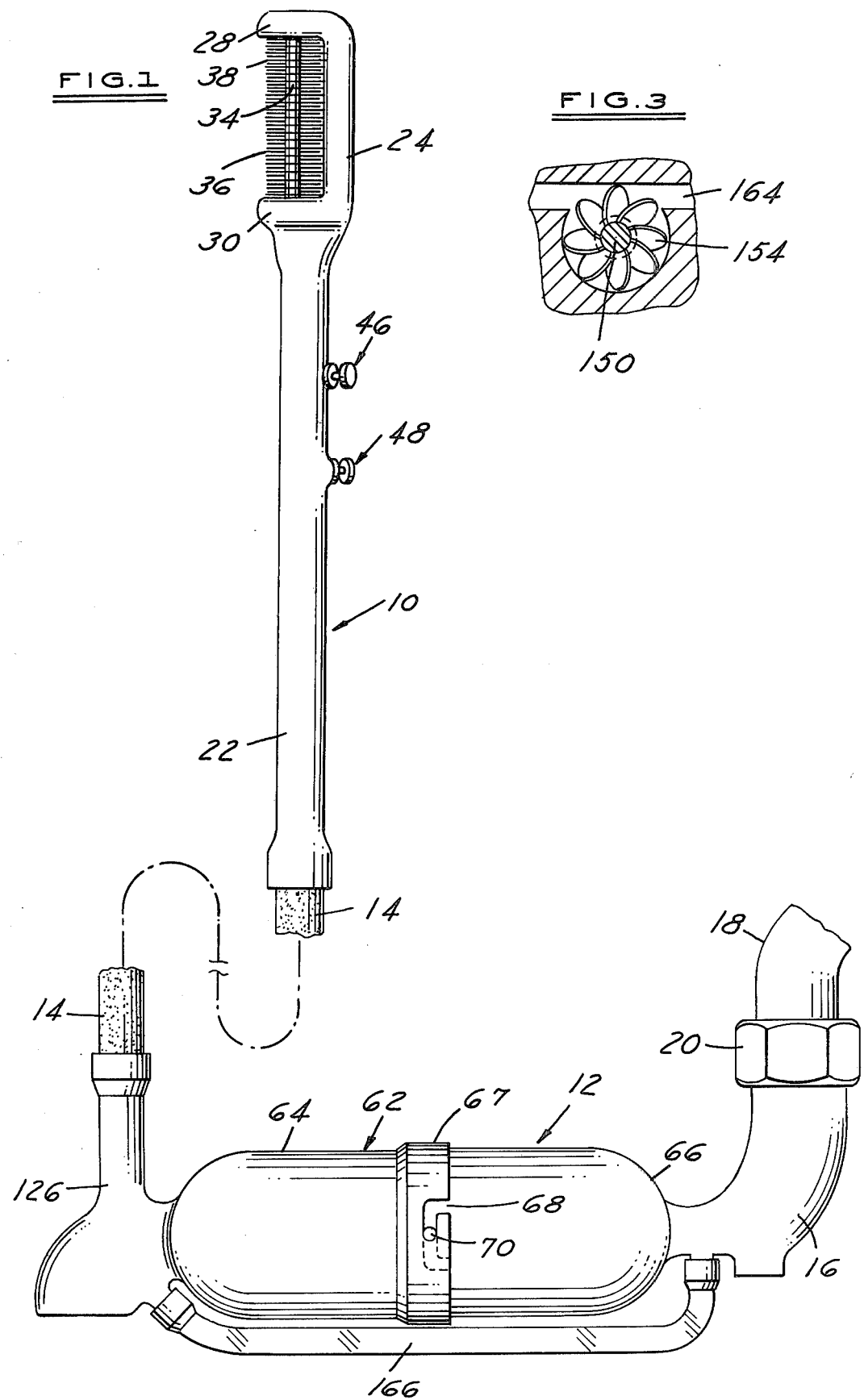

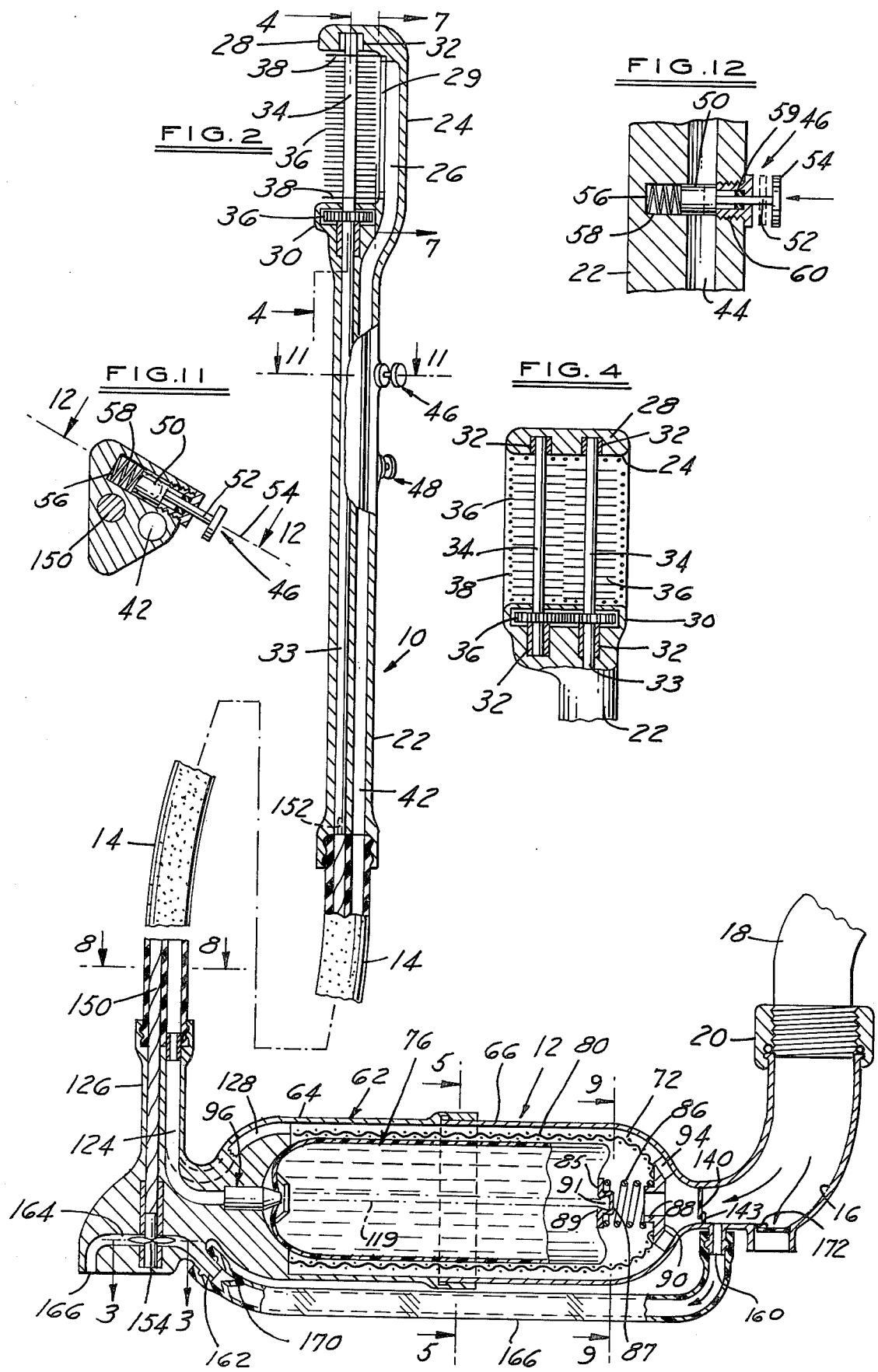

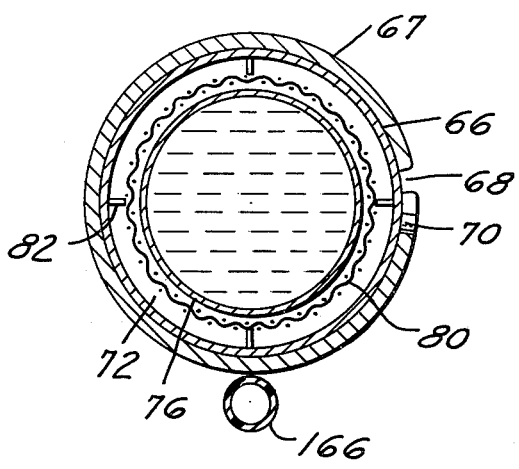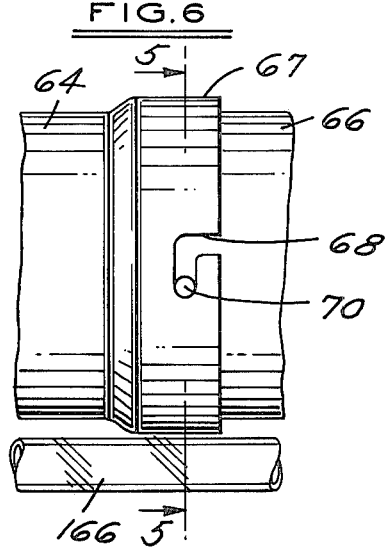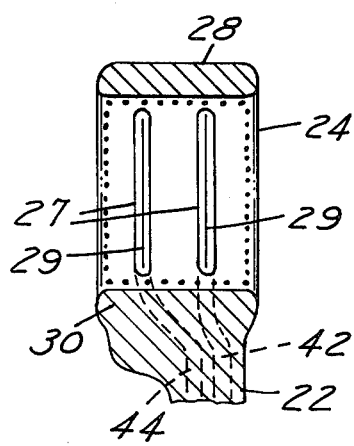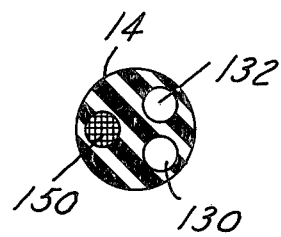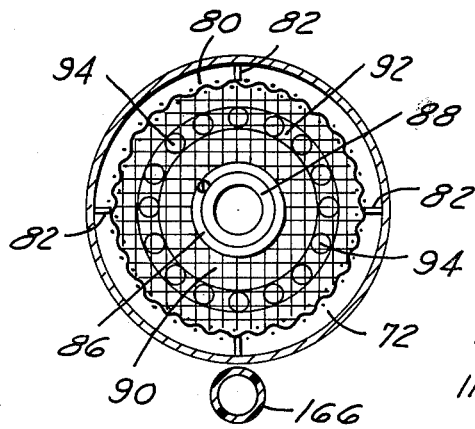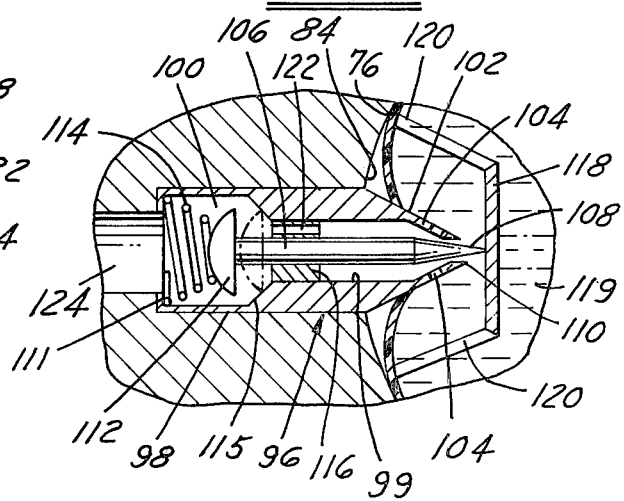

WATER-POWERED TOOTHBRUSH WITH DENTIFRICE ATTACHMENT

SUMMARY OF THE INVENTION

The tooth-brushing device of this invention is designed to utilize the pressure of water from an ordinary household tap or faucet to drive one or more rotary brushes, and also to deliver both dentifrice and water to the rotating brushes. Not only are the brushes power driven by a readily available, practically free source of power, namely, the pressure of water from the faucet, but the application of dentifrice and/or water to the brushes is accomplished by the touch of a button. This may be done even while the teeth are being brushed.

In the specific embodiment of the invention about to be described, a cartridge unit is provided having means for supporting a bag or tube of dentifrice. When the water faucet is turned on, the pressure of water entering the cartridge unit squeezes dentifrice from the tube. The dentifrice is conducted to the rotating brushes under the control of a manually operable valve located on the toothbrush in a convenient position. A separate passage delivers the water to the rotating brushes and this passage is also under the control of a conveniently located manually operable valve.

The cartridge unit supports a rotatable impeller which is driven by the tap water. This impeller is operably connected to the rotating brushes. The drive from the impeller to the rotary brushes is preferably a flexible shaft supported in the cable which also contains the water and dentifrice passages.

The dentifrice bag or tube is initially a sealed member to protect its contents from contamination. When properly installed in the cartridge, this tube is pierced by a cartridge needle so that the contents may be squeezed out into the dentifrice passage, and means on the tube are provided to open a normally closed valve in the end of the dentifrice passage to make the unit ready for use. This dentifrice tube may be removed and replaced when the dentifrice is used up.

IN THE DRAWINGS

FIG. 1 is an elevational view of a toothbrushing device including the brushing unit and cartridge unit, constructed in accordance with my invention.

FIG. 2 is a sectional view of the device shown in FIG. 1.

FIG. 3 is a fragmentary sectional view taken on the line 3—3 in FIG. 2.

FIG. 4 is a fragmentary sectional view taken on the line 4—4 in FIG. 2.

FIG. 5 is a sectional view taken on the line 5—5 in FIGS. 2 and 6.

FIG. 6 is an enlarged elevation of a portion of the structure shown in FIG. 1.

FIG. 7 is a fragmentary sectional view taken on the line 7—7 in FIG. 2.

FIG. 8 is a sectional view taken on the line 8—8 in FIG. 2.

FIG. 9 is a sectional view taken on the line 9—9 in FIG. 2.

FIG. 10 is an enlarged fragmentary sectional view of a portion of FIG. 2.

FIG. 11 is a sectional view taken on the line 11—11 in FIG. 2.

FIG. 12 is a sectional view taken on the line 12—12 in FIG. 11.

Referring now more particularly to the drawings, the brushing device comprises a brushing unit 10 and a cartridge unit 12 connected together by a flexible cable 14. The cartridge unit has a tube 16 at one end adapted to be releasably connected to a water faucet 18. In this instance, the tube 16 is connected to the faucet by a nut 20 rotatably connected to the end of the tube and threadedly connected to the faucet, but it should be understood that any suitable means to make a releasable connection may be employed.

The brushing unit 10 is preferably in the general shape and form of an ordinary toothbrush having an elongated shank 22 provided with a brush head 24 at one end. The brushing unit or toothbrush 10 may be made of any suitable material such, for example, as a hard plastic. The shank 22 should be of a length to fit comfortably in the hand.

The brush head 24 when viewed in side elevation is generally C-shaped as shown. The ends 28 and 30 of the C-shaped head provide supports for bushings 32 in which the ends of a pair of brush shafts 34 are rotatably supported. These brush shafts are disposed in laterally spaced parallel relation and extend generally lengthwise of the toothbrush. These brush shafts 34 are detachable as by means of a spring-return device in each of the bearings 32, so that the toothbrush assembly may be available for use by more than one person. If desired, instead of making the brush shafts 34 detachable, the entire brush head assembly could be disconnected from the brush handle by means of a detachable connection such as a slip-on - slip-off means, and another brush head could thus be connected allowing for more than one person to use the tooth brushing device. Each shaft has a plurality of brushing bristles 36 radiating therefrom. One of the shafts has a shaft extension 33 which extends through the shank of the toothbrush to be rotated in a manner to be described hereinafter. Gearing 36' connects the two shafts so that they rotate simultaneously in opposite directions when driven, thus producing counterrotation of the brushes away from the gums.

A series of stationary bristles 38 surround the rotating bristles. These stationary bristles project outward from the base 24 of the C-shaped head, or to the left as viewed in FIGS. 1 and 2. Such stationary bristles project outward sufficiently to extend substantially flush with the rotating bristles. The purpose of the stationary bristles is to prevent water and dentifrice from spraying laterally when the shaft-mounted bristles are rotated while also continuing to perform their present toothbrushing function.

There is a water passage 42 in the shank of the toothbrush. There is also a dentifrice passage 44 in the shank of the toothbrush. These passages communicate with the cable 14 at the end of the shank opposite the head to receive water and dentifrice in a manner to be described more fully hereinafter. Such passages 42 and 44 terminate in outlet ports 27 directly over the shafts 34. Ports 34 are normally closed by one-way lip valves 29 which permit flow only in an outward direction toward the brush shafts. Thus these passages will not be contaminated by reverse flow.

The water and dentifrice passages are controlled by manually operable valves 46 and 48 located on the shank of the toothbrush in convenient positions to be operated by a finger or thumb of the user during brushing. The valves 46 and 48 are identical so that a description of one will suffice for both. As shown in FIGS. 11 and 12, the valve 46 comprises a plunger 50 to which a stem 52 is attached. The stem has a head 54 on the outside of the toothbrush shank which may be depressed to operate the valve. A compression spring 56 in a chamber 58 within the shank normally presses the plunger 50 to the position shown in FIGS. 11 and 12 in which it blocks the passage 44. In this position, the plunger 50 bears against the hollow stud 60 which is threaded into the shank 22 and serves as a quide for the valve stem 52. When the valve stem is depressed, the plunger 50 moves to the left in FIGS. 11 and 12, into the spring chamber 58. In this position, the passage 44 is opened to permit the flow of dentifrice. A suitable seal 59 may be provided around stem 52.

It will be understood that passages 42 and 44 are thus normally closed by the valves 46 and 48, but may be opened by simple finger pressure on the valve stem. These valve stems are close enough together so that they may be simultaneously operated if desired.

The cartridge unit 12 comprises an elongated hollow housing 62 formed in two sections 64 and 66. These two sections are releasably connected together by any suitable means such, for example, as a bayonnet type lock. As shown in FIG. 6, the section 62 has an enlarged bell-mouth 67 formed with an L-shaped slot 68. The adjacent end of the other section 66 fits in the bell-mouth 66 and has a radially outwardly extending pin 70. To assemble the pin 70 in the slot 68 and thus releasably connect the parts 64 and 66 of the housing 62 together, the parts 64 and 66 are simply moved towards one another and counterrotated.

The elongated chamber 72 formed in the housing 62 is provided to contain the dentifrice holding means which in this instance comprises a simple bag or tube 76 of thin walled flexible material such as rubber or plastic. Chamber 72 communicates at one end with tube 16 which attaches to the faucet. The tube 76 is an elongated, continuous, sealed hollow sausage-shaped member. It is sufficiently strong to permit ordinary handling without breaking, but at least one end is capable of being pierced by a needle to prepare it for use when properly installed in the cartridge unit, as will become more apparent hereinafter.

The bag or tube 76 of dentifrice is supported lengthwise within the chamber 72 by the elongated tubular screen support 80. The screen 80 is open at the end 81 to permit the tube 76 to be inserted. The opposite end 83 of the screen is open but necked down somewhat as seen in FIG. 2 to conform to the contour of the end of tube 76 and to contact support 90 described more fully hereinafter. The screen 80 is sufficiently self-supporting to retain its cylindrical form and support the dentifrice tube in the position shown. There are ribs 82 which project inwardly from the walls of the housing sections 62 and 66 to support the screen 80 in spaced substantially concentric relation within the housing as shown in FIGS. 5 and 9.

When thus supported in the housing by the screen 80, one end of the tube 76 engages the concave inner end 84 of the housing. The other end of the tube is engaged under pressure by a plate 85 on one end of a compression coil spring 86. The opposite end of the spring 86 is secured to the tubular boss 88 on the spring support 90 which is secured to the end wall of the housing section 66 by a ring-shaped flange 92 having a circular series of spaced passages 94 to permit the flow of water from tube 16 into chamber 72. The plate 85 is pressed by spring 86 against one end of the dentifrice tube to maintain the opposite end firmly in contact with the concave surface 84 in the housing section 64. The necked down end 83 of the screen engages the support 90 in the area surrounding the boss 88.

The plate 85 has a central bulb-shaped recess 87 provided with a relatively narrow neck 89. Tube 76 has a solid thickened knob 91 which integrally connects to the tube at a reduced neck. This knob enters the recess in the assembled position of FIG. 2 to retain the connection between the tube and plate as the dentifrice is used.

A piercing mechanism 96 is provided to pierce the end of the dentifrice tube 76 when properly installed in the housing. This piercing mechanism comprises a tubular punch 98 and a needle 106 in the passage 99 of the punch. The passage has an enlarged chamber 100 at one end. A tapered nose 102 on the punch projects into the chamber 72 through the concave wall 84. Fluid passages 104 are provided in the nose of the punch. The piercing needle 106 is slidably supported within the punch passage by bushing 116 for longitudinal movement. This needle has a sharp end 108 which projects through the hollow tip 110 in the nose of the punch. Before the tube 76 is installed in the housing, the needle projects from the punch farther than illustrated in FIG. 10, to a position in which the head 112 of the needle engages the annular wall 115 of chamber 100 to close the passage through the punch, thereby preventing any dentifrice loss from backflow thereinto. The dentifrice passage 44, from the punch to the one-way valve in the brush head, will thus be maintained filled and ready for instant operation when a full dentifrice tube 76 is installed. The needle is pressed to this closed position by the compression spring 114 supported against the inturned annular flange 111 of the chamber 100.

It will be noted that the tube 76 has within it a transverse barrier plate 118 secured in spaced relation to one end of the tube by two or more legs 120 affixed to the tube wall. This plate is located so as to engage the point of the needle when the tube 76 is fully installed in chamber 72 to retract the needle to the FIG. 10 position in which the needle head 112 disengages wall 115, thereby to open the punch passage for the flow of dentifrice. In this connection, it will be noted that the bushing 116 has one or more ports 122. The tube end may be very thin so as to be instantly pierced by the needle when installed, or it may be somewhat thicker so that it will first retract the needle at least partially before being pierced, after which of course the needle will be held retracted by plate 118.

FIGS. 2 and 10 show a modification in dotted lines consisting of a rod 119 within dentifrice tube 76 secured at one end to the knob 91 and at the other end to barrier plate 118. This rod preferably is disposed on the longitudinal center line of the dentifrice tube and is provided to prevent the tube from shrinking in a lengthwise direction as dentifrice is consumed. Such shrinking of the tube could cause the barrier plate 118 to move away from the needle 106 allowing the same to close unintentionally. While not believed absolutely necessary, since the water pressure on the tube 76 produces primarily a diametral rather then a longitudinal reduction in the tube as dentifrice is expelled, nevertheless the rod 119 is recommended in some cases as an added safeguard to hold needle 106 open.

A passage 124 in the housing extends from the chamber 100 of the punch through a housing extension 126.

The housing also has a passage 128 which extends from chamber 72 through the housing extension 126. These passages 124 and 128 lead through passages 130 and 132 in the cable 14 to the passages 44 and 42 in the toothbrush. As seen in FIG. 2, the ends of the cable are firmly secured to the extension 126 of the cartridge unit and the end of the shank 22 of the toothbrush. There is a one-way valve 140 between the tube 16 and chamber 72 of the cartridge unit, permitting flow only in a direction from the water faucet into the chamber. The valve 140 may be of any suitable construction, but is here shown as a flexible leaf 141 the free end of which normally seals against abutment 143.

The shaft extension 33 of one of the rotary brushes is rotated by a flexible shaft 150 which has a non-rotating connection 152 at one end with the end of the shaft extension, and at the other end extends into the extension 126 of the cartridge unit. This flexible shaft 150 has an impeller 154 on one end within the cartridge unit. The cartridge unit has a water outlet 160 from the tube 16 and a water inlet 162 adjacent the impeller and connected thereto by a passage 164. A flexible tube 166 connects the outlet 160 to the inlet 162 so that water from the faucet can bypass the chamber 72 of the cartridge unit and flow directly across the impeller and then return to the washbasin through the outlet port 166. This flow of water past the impeller rotate the shafts 150 and 33 to cause the brushes to turn in opposite directions away from the gums. A suitable one-way valve 170 in tube 166, similar to valves 29, permits flow of water only in a direction toward the impeller 154.

There is a relief valve 172 in the tube 16 of the cartridge unit, the purpose of which is to discharge water into the basin in the event that the pressure becomes too great for safe operation. This relief valve may be of any suitable construction, such, for example, as the valve 140.

In use, the tube 16 of the device is attached to the water faucet 18 as shown in FIG. 2, and the water is turned on. The water flows through tube 166 to turn impeller 154 and counterrotate the brushes.

Water from the tube 16 enters the chamber 72 past valve 140 and flows through passages 128, 132 and 42 to the normally closed valve 48. When the stem of this valve is depressed, water will flow through ports 27 past valve 29 and will discharge upon the rotating brushes.

The pressure of the water in chamber 72, particularly when the water valve 48 is in its normally closed position, is sufficient to squeeze the bag or tube 76 and force dentifrice through the punch mechanism 96 and passages 124, 130 and 44 to the normally closed valve 46. When this valve is opened by depressing the valve stem, the pressure on the dentifrice tube 76 will cause the dentifrice to be squeezed onto the brushes through port 27 past valve 29. Both valves 46 and 48 may be opened at the same time if desired.

As the supply of dentifrice in tube 76 is consumed, the tube will begin to collapse under the pressure of water in chamber 72. The screen support 80 however will not collapse since it is a porous member. The spring 86 will maintain the end of the tube firmly against the concave wall 84 of the chamber. The knob and recess connection between the tube 76 and plate 85 will prevent the tube end from pulling away from spring 86 and thereby prevent some other part of the tube from contacting and being pierced by the piercing mechanism 96.

When it is desired to remove and replace a used-up dentifrice tube, the sections 64 and 66 of the housing 62 are separated and the screen 80 and tube 76 are removed. The old tube may be removed by permitting it merely to drop from the open end 81 of the screen. A replacement dentifrice tube may then be inserted into the open end. The screen and tube are installed in the housing chamber after which the housing sections are reunited. When the fresh tube and screen are inserted in the housing section 66, the end of the tube having the knob 91 should be pressed down on the plate 85 to engage the knob firmly in the recess 87. Then the sections 64 and 66 of the housing are brought together and locked. During the time that no dentifrice tube is in the chamber, the needle 106 of the punch mechanism is in the extended dotted line position of FIG. 10 so that its head seats against wall 115 to close the passage through the punch mechanism and thereby prevent flow in either direction in the dentifrice passages. When a dentifrice tube 76 is properly installed as shown in FIG. 2 within the chamber with spring pressure on one end, its opposite end will be pierced by the needle 106 and the opening in the pierced end will be enlarged by the nose of the punch as shown in FIG. 10. The plate 118 will retract the needle 106 to lift its head 112 away from the wall 115 so that dentifrice can flow from the dentifrice tube 76, through the hollow tip of the punch, the ports 104 in the punch, through the punch passage, and into the dentifrice passages in the cartridge unit, the cable and the toothbrush 10.

It will be understood that the tube 166 is sufficiently flexible to enable the housing sections 64 and 66 to be separated from one another far enough to permit removal and replacement of the tube 76 and screen support 80.

It will be noted that the valves 29 and 140 retain water in the cartridge unit and toothbrush so that the device will operate instantly when the tap is turned on. There is no delay before operation commences because the passages are filled with water and have not drained. The presence of water in the cartridge keeps the dentifrice passage, from the dentifrice tube to the valve in the brush head, filled with dentifrice likewise for instant operation.

The construction provides for counterrotation of the brushes away from the gums. Thus the user can move the brush head in the usual manner back and forth in a horizontal plane, while avoiding any abrasion of the gums at the point where they join the teeth.

It will be understood that while in the foregoing description the tube 76 has been referred to as containing dentifrice, such tube may contain any other oral substance such, for example, as a mouth wash. It will also be understood that instead of having only one tube 76 for holding a single oral substance, the cartridge unit may be designed to support two or more such tubes, one of which may, for example, hold a dentifrice, another an oral mouth wash, and another distilled water or mineral water or such, in which event additional valve controlled passages from the tubes holding these additional oral substances would be provided in the toothbrush to the brush head.

The cartridge unit may be designed to be connected to a lengthened conduit 16 so that it can be attached to a wall or other firm support above the basin for example. Such an arrangement might be desirable particularly if the cartridge unit were designed to carry more than one tube 76, because of its additional bulk and weight. When supported in this manner above the basin it might be necessary to extend the channel 64 so that the water exiting from the cartridge unit can be directed back into the basin.

It will be understood of course that instead of the screw type connection 20, a simple slip-on arrangement may be substituted.

What I claim as my invention is:

1. A tooth-brushing device comprising a brushing unit having a rotatable shaft to which bristles are secured, a cartridge unit having means for holding an oral substance, a first passage from said holding means to said brushing unit, a water passage to said brushing unit, said water passage having means releasably attachable to a water faucet, a rotatable impeller operably connected to said shaft, a branch line from said water passage to rotate said impeller by the flow of water in said branch line and thereby rotate said shaft, said holding means comprising a squeezable tube releasably mounted in a chamber in said cartridge unit, whereby the oral substance can be expelled from said tube by squeezing, said chamber being in communication with said water passage so that the pressure of water in said water passage will squeeze said tube.

2. The tooth-brushing device defined in claim 1, including separate valve means normally closing said passages and individually manually operable to open the same.

3. A tooth-brushing device comprising a brushing unit having bristles, a cartridge unit having means for holding an oral substance, a first passage from said holding means to said brushing unit, and a water passage to said brushing unit, said water passage having means releasably attachable to a water faucet, said holding means comprising a squeezable, disposable tube, means for releasably installing said tube in said cartridge unit, valve means for closing said first passage, and means on said tube operable when said tube is installed in said cartridge unit for opening said valve means.

4. The tooth-brushing device defined in claim 3, wherein said tube is installed in a chamber in said cartridge unit, said chamber is in communication with said water passage so as to be subject to the pressure of water in said water passage and said tube is thus squeezed thereby.

5. The tooth-brushing device defined in claim 4, including separate valve means normally closing said passages and individually, manually operable to open the same.

6. The tooth-brushing device defined in claim 5, including a shaft rotatably mounted on said brushing unit and to which said bristles are secured, an impeller operably connected to said shaft to rotate the same, a branch line from said water passage to turn said impeller by the flow of water in said branch line, and a second shaft with bristles rotatably mounted on said brushing unit and geared to said first-mentioned shaft thus producing counterrotation of the brushes away from the gums.

7. The tooth-brushing device defined in claim 6, including stationary bristles secured to said brushing unit along the sides of said shafts to reduce spray from said shaft-mounted bristles when said shafts rotate.

8. A tooth-brushing device comprising a brushing unit having bristles, a cartridge unit having means for holding an oral substance, a first passage from said holding means to said brushing unit, and a water passage to said brushing unit, said water passage having means releasably attachable to a water faucet, said holding means comprising a squeezable, disposable tube, means releasably installing said tube in said cartridge unit, piercing means automatically operative to pierce said tube upon initial installation thereof to allow the oral substance to flow therefrom into said first passage, valve means for closing said first passage, and means on said tube operative upon initial installation thereof to open said valve means.

9. A tooth-brushing device comprising a brushing unit having bristles, a cartridge unit having a tube for holding an oral substance, a first passage from said tube to said brushing unit, a water passage to said brushing unit, said water passage having means releasably attachable to a water faucet, said tube being disposed in a chamber in said cartridge unit and being squeezable to enable forcing the oral substance from said tube to said brushing unit, said chamber being in communication with said water passage so that said tube is subject to the pressure of water in said water passage to be squeezed thereby, and various valve means which permit the flow of the oral substance and water in said passages in the direction of said brushing unit only and prevent drainage of said passages to keep said passages filled for instant operation when the water faucet is turned on.

10. A tooth-brushing device comprising a brushing unit having bristles, a cartridge unit having a tube for holding an oral substance, a first passage from said tube to said brushing unit, a water passage to said brushing unit, said water passage having means releasably attachable to a water faucet, said tube being disposed in a chamber in said cartridge unit and being squeezable to enable forcing the oral substance from said tube to said brushing unit, said chamber being in communication with said water passage so that said tube is subject to the pressure of water in said water passage to be squeezed thereby, and a porous cylindrically shaped member for holding said tube within said chamber, one end of said porous member being open to permit the insertion and removal of sid tube and the other end of said porous member being shaped to conform to the corresponding end of said tube.

11. A tooth-brushing device comprising a brushing unit having bristles, a cartridge unit having a tube for holding an oral substance, a first passage from said tube to said brushing unit, a water passage to said brushing unit, said water passage having means releasably attachable to a water faucet, said tube being squeezable and releasably mounted in a chamber in said cartridge unit whereby said oral substance can be expelled from said tube by squeezing, said chamber being in communication with said water passage so that the pressure of water in said water passage will squeeze said tube.

12. A tooth-brushing device comprising a brushing unit having bristles, a cartridge unit having a container for an oral substance, a passage from said container to said brushing unit, valve means for closing said passage, means for releasably installing said container in said cartridge unit, and means on said container operable when said container is installed in said cartridge unit for opening said valve means.

13. A tooth-brushing device comprising a brushing unit having bristles, a cartridge unit having means for holding an oral substance, a first passage from said holding means to said brushing unit, a water passage to said brushing unit, said water passage having means releasably attachable to a water faucet, and various valve means which permit the flow of the oral substance and water in said passages in the direction of said brushing unit only and prevent drainage of said passages to keep said passages filled for instant operation when the water faucet is turned on.

14. A tooth-brushing device comprising a brushing unit having bristles, a cartridge unit having a tube for holding an oral substance, a first passage from said tube to said brushing unit, a water passage to said brushing unit, said water passage having means releasably attachable to a water faucet, said tube being disposed in a chamber in said cartridge unit and being squeezable to enable forcing the oral substance from said tube to said brushing unit, said chamber being in communication with said water passage so that said tube is subject to the pressure of water in said water passage to be squeezed thereby, and a porous cylindrically shaped member for holding said tube within said chamber.

15. A tooth-brushing device comprising a brushing unit having a rotatable shaft to which bristles are secured, a passage for delivering an oral substance to an outlet port directly opposite and in close proximity to said bristles to deposit the oral substance on said bristles, a lip valve normally closing said outlet port, means for forcing said oral substance in said passage through said lip valve, and means for rotating said shaft whereby said bristles pick up the oral substance forced through said lip valve.

* * * * *